(12) United States Patent
Kim et al.

(10) Patent No.: US 8,607,615 B2
(45) Date of Patent: Dec. 17, 2013

(54) MICROFABRICATED THERMAL MODULATOR FOR COMPREHENSIVE 2D GAS CHROMATOGRAPHY

(75) Inventors: Sung Jin Kim, Ann Arbor, MI (US); Katsuo Kurabayashi, Ann Arbor, MI (US); Kensall D. Wise, Ann Arbor, MI (US); Edward T. Zellers, Ann Arbor, MI (US); Bruce P. Block, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 540 days.

(21) Appl. No.: 12/906,357

(22) Filed: Oct. 18, 2010

(65) Prior Publication Data

US 2011/0088452 A1   Apr. 21, 2011

Related U.S. Application Data

(60) Provisional application No. 61/252,813, filed on Oct. 19, 2009.

(51) Int. Cl.
*G01N 30/30* (2006.01)

(52) U.S. Cl.
USPC .................................. 73/23.42; 95/86; 95/87

(58) Field of Classification Search
USPC ........ 96/101, 103, 104, 106; 73/23.42; 95/86, 95/87
See application file for complete search history.

(56) References Cited

U.S. PATENT DOCUMENTS

| | | | | |
|---|---|---|---|---|
| 5,135,549 A | * | 8/1992 | Phillips et al. | 95/8 |
| 5,196,039 A | * | 3/1993 | Phillips et al. | 210/656 |
| 7,147,695 B2 | * | 12/2006 | Mitra | 96/101 |
| 7,273,517 B1 | * | 9/2007 | Lewis et al. | 96/101 |
| 7,284,409 B2 | * | 10/2007 | Hasselbrink et al. | 73/23.42 |
| 2001/0037727 A1 | * | 11/2001 | Ledford et al. | 95/87 |
| 2005/0268693 A1 | | 12/2005 | Hasselbrink et al. | |
| 2007/0029477 A1 | | 2/2007 | Miller et al. | |
| 2008/0302959 A1 | | 12/2008 | Amirav | |
| 2009/0173146 A1 | | 7/2009 | Pursch et al. | |

* cited by examiner

*Primary Examiner* — Daniel S Larkin
(74) *Attorney, Agent, or Firm* — Harness, Dickey & Pierce, P.L.C.

(57) ABSTRACT

A two-dimensional gas chromatography system having first and second separation columns, a thermal modulator disposed between the first and second columns and having a plurality of stage channels, and a micro heater monolithically integrated in the thermal modulator. The thermal modulator is operable to trap and focus gas/vapor species within the plurality of stage channels upon cooling and release the gas/vapor species to the second column upon heating by the micro heater.

18 Claims, 1 Drawing Sheet

MICROFABRICATED THERMAL MODULATOR FOR COMPREHENSIVE 2D GAS CHROMATOGRAPHY

CROSS-REFERENCE TO RELATED APPLICATIONS

This application claims the benefit of U.S. Provisional Application No. 61/252,813, filed on Oct. 19, 2009. The entire disclosure of the above application is incorporated herein by reference.

GOVERNMENT INTEREST

This invention was made with government support under Grant Nos. NNG-06GA89G and EEC9986866 awarded by the Aeronautics and Space Administration and the National Science Foundation, respectively. The government has certain rights in the invention.

FIELD

The present disclosure relates to thermal modulators and, more particularly, relates to a robust, high-speed miniaturized thermal modulator for comprehensive 2D gas chromatography.

BACKGROUND

This section provides background information related to the present disclosure which is not necessarily prior art.

Comprehensive two-dimensional gas chromatography (GC×GC) is an analytical technique used to separate and detect the components of complex mixtures of volatile organic compounds. Unlike standard gas chromatography, which uses a single column for vapor separation, GC×GC couples a first-dimension column to a relatively short second-dimension column whose retention properties are complementary to those of the first-dimension column. Through a junction-point modulator between the two columns, mixture components partially separated on the first dimension column are focused and reinjected as a series of narrow pulses onto the second-dimension column. This results in an increase in peak capacity (i.e., the number of compounds that can be separated in a given analysis) and in sensitivity as a 2-D chromatogram is produced. The term 'comprehensive' refers to the fact that none of the originally injected sample is lost during the modulated separation process.

A pneumatic or thermal modulator (TM) is used at the interface between the two columns, with the latter generally providing a greater degree of sensitivity enhancement. A thermal modulator relies on low temperature to trap and focus the analytes as they elute from the first-dimension column, and then reintroduces them to the second-dimension column by rapid heating. By repeating this operation in rapid succession, the vapor profile is parsed into several segments, each of which is eluted through the second-dimension column. Thermal modulators, which are used in conventional bench-scale GC×GC systems, can be grouped into a thick stationary-phase film modulator and a cryogenic modulator. In the former, analytes are focused in a small section of capillary by the polymeric phase at ambient temperature. The latter uses a cryogenically cooled fluid such as $CO_2$, $N_2$, or air.

The two types of thermal modulators commonly use conductive or convective heating techniques to rapidly raise the temperature of the modulator. However, those macro-scale thermal modulators relying on cryogenically cooled fluids are resource intensive and/or demand a large amount of refrigeration work (e.g., ~10 kJ for a cooling cycle of ~5 s). Furthermore, power dissipation for typical heating devices can be on the order of 1 kW. Numerous efforts have been made to develop gas chromatography prototypes containing microfabricated components (µGC). These miniaturized systems and their components can operate at relatively low power; however, the lengths of the columns employed are inherently limited, with typical columns ranging in length from 0.5 to 3 metres. Accordingly, this places an inherent limit on the peak capacity. A µGC system incorporating two-dimensional gas chromatography (i.e., µGC×µGC) is a promising approach to overcome this limitation. Although a preliminary report has recently been described on the use of pneumatic modulation in a µGC×µGC system, there has yet to be a report on a microfabricated thermal modulator (µTM) for µGC×µGC applications. To be effective, the microfabricated thermal modulator (µTM) must span a broad range of temperature (e.g. −50 to 250° C.) at a very high rate (>1000° C. s$^{-1}$, ideally during both heating and cooling).

SUMMARY

This section provides a general summary of the disclosure, and is not a comprehensive disclosure of its full scope or all of its features.

The present teachings disclose a microfabricated thermal modulator (µTM), which plays a critical role in a comprehensive two-dimensional gas chromatography (GC×GC) system. The GC×GC operation requires the use of two columns (i.e., conduits) to separate highly complex mixtures of organic vapor/gas compounds based on differences in their both volatility and polarity. In the thermal modulator (TM) between the two columns, the flow speed of gas/vapor species is highly dependent on the temperature. At low temperature, the TM traps and focuses the species from the first column; at high temperature, it reintroduces them to the second column by cyclic high-speed temperature modulation to dissect their profiles into narrow-band cuts. These functions can prevent recombination and elution-order change of the species when the species move from the first to the second column. The device is the first miniaturized thermal modulator based on micro-electro-mechanical (MEMS) technology. The microfabricated thermal modulator (µTM) developed in accordance with the principles of the present teachings will further enable future development of a low-power, low-cost, ultraportable micro-scale GC×GC system (e.g., the use of microfabricated first- and second-dimension columns).

Previously reported modulator designs used a bulky, rotating, slotted-heater (or a cryojet of low-temperature coolant gas) that periodically passes along a segment of constantly cooled (or heated) TM channel for the thermal modulation. However, the conventional TMs lack mechanical fidelity, require a large amount of consumable coolants, or are power intensive. In comparison, the microfabricated thermal modulator (µTM) of the present teachings has no moving parts and uses no consumable coolants. The device is based on a two-stage design, which achieves very sharp sample pulses (i.e. signal enhancement) and low sample losses (e.g., due to breakthrough, see below). Integrated stationary on-chip micro heaters are utilized for heating the micro stage channels. The entire device is attached to a solid-state thermoelectric cooler maintained at low temperature with a 1-100 µm air gap, such as a 20 µm air gap. In some embodiments, the silicon channels of each stage are fabricated using deep reactive ion etching (DRIE) and sealed with a thin cover member.

Notably, the device exhibits fast thermal response and low power consumption due to its drastically smaller size and high thermal isolation.

According to the principles of the present teachings, a two-dimensional gas chromatography system is provided having first and second columns, a thermal modulator disposed between the first and second columns and having a plurality of stage channels, and a micro heater operably coupled with the thermal modulator. The thermal modulator is operable to trap and focus gas/vapor species within the plurality of stage channels upon cooling and release the gas/vapor species to the second column upon heating by the micro heater.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
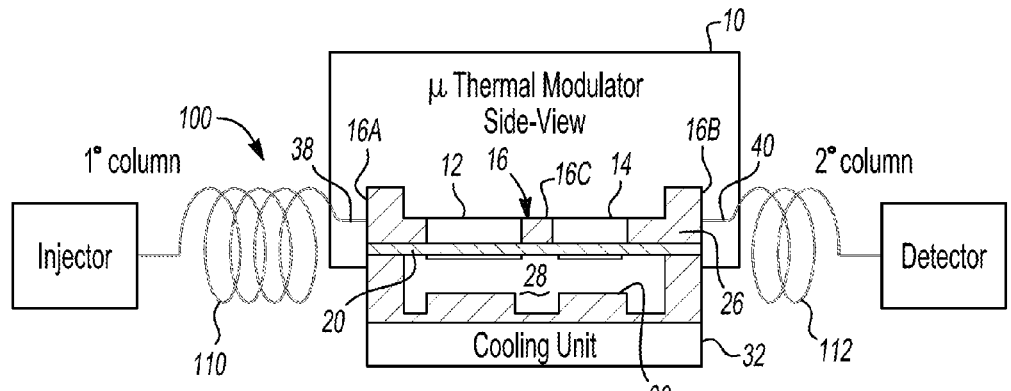
FIG. 1 is a schematic view illustrating a comprehensive 2D gas-chromatography (GC×GC) system incorporating a microfabricated thermal modulator (µTM) between two columns.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

According to some embodiments of the present disclosure, the design, fabrication, modeling, and testing of a microfabricated thermal modulator (µTM) 10 that incorporates two series-coupled serpentine Pyrex-on-Si micro channel stages that are cyclically cooled to trap and focus vapors and then sequentially heated to desorb them are provided. According to these teachings, two-stage modulation is adopted where analytes trapped in the first stage are thermally released into the (cooled) second stage for additional focusing prior to injection into the second-dimension column of the two-dimensional gas chromatography system. In addition, the second stage is not heated until the first stage has cooled to a temperature sufficient for trapping. This alternative heating and cooling of these stages helps to avoid 'breakthrough', whereby a sample is lost due to incomplete trapping during thermal transitions, which is a potential problem with single-stage modulator designs.

An emphasis is placed on three design parameters that govern the heat capacity of the device structure of the present teachings and the rate at which heat energy is transported between stages and from each stage to the environment: (1) the thickness of the cover member that seals the silicon micro channel stages of the microfabricated thermal modulator; (2) the air gap between the cooling unit and the microfabricated thermal modulator; and (3) the interconnection channel (IC) that connects the two stages and the rim. The effects of varying these parameters on the device performance are discussed herein, where the trade-off between the heating-cooling cycle speed and the power requirement as well as the thermal crosstalk between the two stages are carefully considered.

According to the principles of the present teachings and with reference to the figures, generally, a microfabricated thermal modulator (µTM) 10 is used in a two-dimensional gas chromatography system (GC×GC) 100 as illustrated in FIG. 1. Specifically, two-dimensional gas chromatography system (GC×GC) comprises a first-dimension column 110 coupled to a second-dimension column 112 whose retention properties are complementary to those of the first-dimension column 110. The microfabricated thermal modulator (µTM) 10 is operably disposed between first-dimension column 110 and second-dimension column 112 wherein mixture components incompletely separated on the first dimension column 110 are received and then focused and reinjected as a series of narrow pulses onto the second-dimension column 112.

Figure 2:
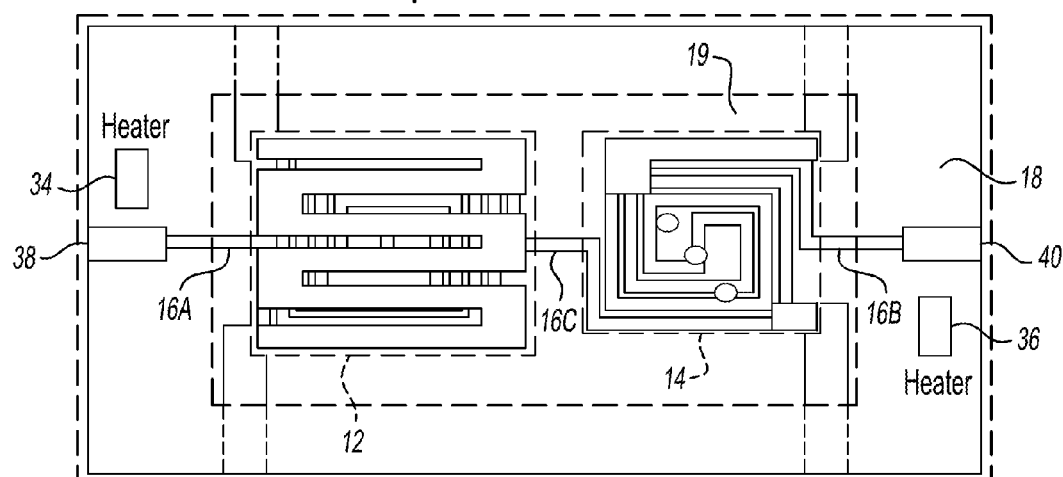
FIG. 2 is a schematic view illustrating the microfabricated thermal modulator according to the principles of the present teachings.
Figure 3:
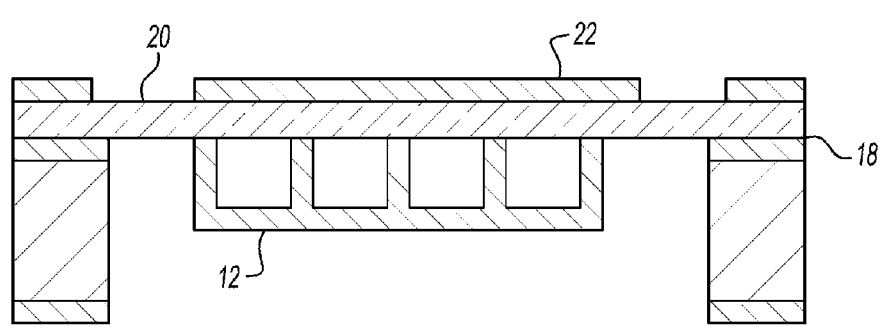
FIG. 3 is a cross-sectional schematic view taken along Line 3-3 of FIG. 2.

With reference to FIGS. 1-3, microfabricated thermal modulator (µTM) 10 comprises a first stage 12 and a second stage 14 being interconnected via an interconnection channel (IC) 16. In some embodiments, by way of non-limiting example, the first stage 12 and the second stage 14 can comprise meander-line micro channels created in boron-doped-Si defining an area of about 2 mm×2 mm or less. In some embodiments, the micro channels of first stage 12 can be 4.2 cm long, with cross-sectional dimensions of 250 µm wide and 140 µm high having a wall thickness in the range of 10-30 µm (or more particularly 10-20 μm). Similarly, second stage 14 can be 2.8 cm long, with cross-sectional dimensions of 250 μm wide and 140 μm high having a wall thickness in the range of 10-30 μm (or more particularly 10-20 μm). The interconnection channel 16 can comprise three segments, such that first segment 16A and second segment 16B connect first stage 12 and second stage 14 each to a rim portion 18, respectively, and third segment 16C connects first stage 12 and second stage 14 together. The three channel segments 16A, 16B, 16C can have the same length, which can vary from 0.5 mm to 1.5 mm in different device designs and the same wall thickness in the range of 10-30 μm (or more particularly 10-20 μm). However, it should be understood that segments 16A, 16B, 16C can also have differing dimensions to tailor specific design criteria.

It should be noted that a reduced material space 19 is disposed between rim portion 18 and first stage 12, second stage 14, and segments 16A, 16B, 16C. This reduced material space 19 reduces the thermal mass of microfabricated thermal modulator (μTM) 10 and further permits improved thermal isolation of first stage 12, second stage 14, and segments 16A, 16B, 16C relative to each other and to rim portion 18.

In some embodiments, as illustrated in FIG. 3. microfabricated thermal modulator (μTM) 10 can further comprise one or more cover members 20 coupled to and sealing each of the first stage 12 and second stage 14 (such as through anodic bonding). It should be noted that, in some embodiments, cover members 20 can be made of PYREX glass. In some embodiments, cover members 20 can be in the range of 1-200 μm thick, or, more particularly, in the range of 40-100 μm thick. Moreover, in some embodiments, the micro channels of first stage 12 and second stage 14 can be made of a polymer or metal and cover member 20 can be made of a dielectric.

Additionally, one or more micro heaters 22 and optional temperature sensors (not shown), made of Ti/Pt for example, can be patterned directly on the cover members 20 for generation of localized heating. Microfabricated Si spacers 26 can be used to create an air gap 28 between the microfabricated thermal modulator (μTM) 10 and the top surface 30 of a thermoelectric cooler 32. In some embodiments, air gap 28 can be in the range of 0-100 μm, or, more particularly, in the range of 22-63 μm. In some embodiments, thermoelectric cooler 32 can be a SP2394 cooler available from Marlow industries. Si spacers 26 can be bonded using an epoxy adhesive onto the cover members 20. In some embodiments, the Si spacers 26 can be separately fabricated by a two-step silicon deep reactive ion etching process, or could be made of another material. Finally, the microfabricated thermal modulator (μTM) 10 can be mounted on a printed circuit board or other substrate and wire bonded for electrical connection.

Still further, in some embodiments, one or more rim heaters 34, 36 can be coupled to rim portion 18 generally adjacent to an inlet 38 and an outlet 40 of microfabricated thermal modulator (μTM) 10. Rim heaters 34, 36 can be used to elevate and/or modulate the temperature of rim portion 18 as it has been found that the elevated temperature of rim portion 18 can advantageously affect the peak sharpness in the chromatogram of the modulated vapor/gas. Through experimental analysis, it was found that use of rim heating a 50-fold peak-height enhancement in 10 ppm n-octane vapor can be realized.

In some embodiments, the internal surface of one or more of the segments 16A, 16B, 16C can be dynamically coated with polydimethylsiloxane (PDMS) from a solution (0.10 g mL$^{-1}$ in 1:1 pentane-dichloromethane) that also contained a thermally activated cross-linking agent, dicumyl peroxide (1 mg mL$^{-1}$). Dynamic coating entails applying a positive pressure of nitrogen gas to a reservoir containing the polymer solution and directing it through the device. Nitrogen flow was maintained for two (2) hours after the solution passed through the device to evaporate the solvent. Cross-linking was achieved by temporarily sealing the inlet and outlet ports of the thermal modulator 10 and heating to 180° C. with the integrated heaters. Although the short capillary sections connected to the device may also be coated during this process, they do not affect the device performance or the chromatographic separation of the analytes significantly.

Operational Discussion

To substantiate the present design, various aspects of the design and/or environment were varied to determine their effect on the operation and optimization of microfabricated thermal modulator (μTM) 10.

Effect of Cover Member Thickness on Thermal Response

To efficiently trap the eluting vapors and introduce them to the second-dimension column 112 in a narrow band, fast cooling and heating are necessary with low heating and cooling power. It was thus an aspect of the present teachings to minimize thermal-response time and heating power required. For practical reasons related to microfabrication, a focus was placed on cover member thicknesses of 40 and 100 μm, and the experimental data was compared to theoretical prediction. Initially, the microfabricated thermal modulator (μTM) 10 was approximately at −55° C. by the cooling unit. When a constant voltage was applied for a 150 ms duration, the first stage 12 was heated and reached its maximum temperature; then it cooled down to −55° C. after cessation of the voltage. As expected, the device with the thinner cover member was raised to a higher temperature for a given applied voltage. It required only 62% of the average power required for the thicker-membrane device (i.e., 6.8 W vs. 11 W) to achieve a temperature of 200° C. For the experimental data, the time evolution of power was directly measured from the applied current and the voltage and, for the theoretical prediction, it was calculated from the electrical resistance and the voltage at the micro heater 22. Then, the average heating powers were obtained from the area of heating power curve divided by the duration of the voltage pulse. It was determined that the thinner cover member also permits a faster cooling response, with the time constant for cooling being about half of that for the device with the thicker cover members (i.e., 0.24 s vs. 0.46 s).

A linear relationship was found between time constant and the cover member thickness. The time constant is proportional to the thermal mass ($M_T$) and is inversely proportional to the thermal conductance ($G_T$) by the heat-transfer terms (i.e. $M_T/G_T$). The cover member thickness generally affects both $M_T$ and $G_T$. Even though the values of heat conduction through the cover member and the interconnection channel 16 change with the cover member thickness, thermal conductance ($G_T$) shows little change because the heat transfer via the air gap 28, which is only governed by the air-gap size, is the dominant term in the heat transfer. As a result, the change of the time constant is mainly dependent on thermal mass ($M_T$). Thus, the time constant is linearly proportional to the thickness of cover member 20.

Effect of Air Gap on Thermal Response

Additionally, the thickness of air gap 28 was studied to determine its effects on the heating and cooling responses of microfabricated thermal modulator (μTM) 10. The thermal response of the first stage 12 for two representative air gaps (22 μm and 63 μm) was measured based upon applying 35 V to the micro heater 22 for 100 ms. Notably, the temperature increase was smaller for the device with the smaller air gap. Accordingly, the power required to reach a maximum temperature of 210° C. was calculated to be 11.5 W with the smaller air gap and 7.2 W with the larger gap. It was also determined that the theoretical average heating-power required for reaching the same maximum temperature of the first stage 12 increases sharply with the decreasing air gap 28.

On the other hand, the narrower air gap 28 resulted in faster cooling. It was found that a narrow air gap 28 enhances the cooling speed at the expense of higher heating power. By way of non-limiting example, it was found that initially setting the air gap 28 small (down to 22 μm) is a practically viable approach because (1) once microfabricated thermal modulator (μTM) 10 is set, it is difficult to change the size of air gap 28 while the power can be easily controlled and (2) the power consumption is found to be still at an acceptable level even for the narrow air gap of 22 μm.

Effect of Air Gap and Interconnection Channel Length on Thermal Crosstalk

Although the heating of one of the stages naturally influences the temperature at the other stage, this thermal crosstalk should be minimized to independently control the temperatures of the two stages 12, 14. To achieve this goal, the air gap was varied from 22 to 38 μm and the length of interconnection channel 16 from 0.5 to 1.5 μm based on theoretical modeling and experimental data indicating that these would provide a reasonable tradeoff between thermal response speed and heating-power consumption, and would also provide acceptable vapor-modulation performance. Specifically, an air gap >40 μm yielded a cooling time from 250 to −50° C. of >1 s, while an air gap <20 μm required >13 W to heat from −55 to 250° C. Also an interconnection channel 16 longer than 1.5 mm resulted in broader vapor peaks because of the large temperature gradient inside the interconnection channel 16.

It was found that the length of interconnection channel 16 affects the thermal crosstalk more than the air gap thickness in these ranges. For a first stage 12 maximum temperature ($T_{max1}$) of 1200° C., the maximum temperature rise of the second stage 14 ($\Delta T_{max2}$) varied from 9 to 11° C. with the air gap varying from 22 to 38 μm for the interconnection channel 16 length fixed at 1.5 mm, whereas $\Delta T_{max2}$ changed from 9 to 19° C. with the interconnection channel 16 length varying from 1.5 mm to 0.5 mm with the air gap fixed at 22 μm. Furthermore, the thermal crosstalk, which is defined as $\Delta T_{max2}/\Delta T_{max1} \times 100\%$, was maintained at 9.2% (at $T_{max1}=200°$ C.) even for the worst case where the interconnection channel 16 length and the air gap were 0.5 mm and 38 μm, respectively.

The dominant effect of the interconnection channel 16C length on the thermal crosstalk can be explained by comparing dissipated thermal energies. The energy-storage rate of the second stage 14 balances with the other heat-transfer parameters. However, it should be understood that the conductive heat transfer between the first stage 12 and second stage 14 via interconnection channel 16C and the heat transfer between the second stage 14 and the thermoelectric cooler 32 via the air gap 28 are the major contributors to the temperature of the second stage 14. Therefore, if one considers these two terms for additional analysis, one can estimate the effects of the air gap 28 and the length of interconnection channel 16C on the maximum temperature rise of the second stage 14 ($\Delta T_{max2}$) by considering dissipated energies rather than energy-change rates, because $\Delta T_{max2}$ represents an energy state determined by the thermal history. Thus, by comparing the ratio of the two dissipated energies at $\Delta T_{max2}$, it was determined that regardless of the values used for the length of interconnection channel 16C and air gap 28, the ratio of the two dissipated energies remain at a value of about 3, indicating that the length of interconnection channel 16C has the greatest effect on thermal crosstalk between first stage 12 and second stage 14.

CONCLUSIONS

It should be appreciated from the foregoing that that a MEMS-based microfabricated thermal modulator (μTM) 10 is provided for use in comprehensive two-dimensional separations of complex mixtures of volatile organic compounds provides several unique advantages. At least some of the unique advantages of the microfabricated thermal modulator (μTM) 10 include (1) low power consumption, where the power is two orders of magnitude smaller than that of the conventional benchtop thermal modulators, (2) low thermal crosstalk between first stage 12 and second stage 14 and between stages 12, 14 and rim portion 18, and (3) no need for cryogenic consumables for cooling. These unique features constitute a significant advantage over current thermal modulator techniques.

As discussed herein, advantage (1) is enabled by the low thermal mass (or alternatively, thermal capacitance) of the microfabricated thermal modulator (μTM) 10. The low thermal mass results from the design incorporating, in some embodiments, small on-chip stages of less than about 2 mm×2 mm in area, a thin channel wall of about 10-20 μm in thickness, and a thin cover member with a thickness of about 40-100 μm. However, in some embodiments, a thin channel wall of about 1-40 μm in thickness, and a thin cover member with a thickness of about 1-200 μm can be used. Also, because of the low thermal conductivity of the cover member, particularly when made as a Pyrex membrane (~1.1 W/m K), the heat generated by the integrated micro heaters 22 is efficiently confined within the stages, thereby resulting in the fast heating performance during the thermal modulation cycle. These miniaturized device features are made possible by the MEMS technology and design of the present teachings.

Advantage (2) is realized by providing a microfabricated interconnection channel (IC) between the two stages, which, in some embodiments, has a channel wall thickness of 10-20 μm and a length of 0.5-1.5 mm. In some embodiments, a channel wall thickness of 1-40 μm and a length of 0.4-2.0 mm can be used. This design enhances high thermal isolation between the stages and between the rim and the stages, so the independent temperature control between the two stages is possible. The rim heaters are constantly turned on during the alternating activation of the stages.

Finally, advantage (3) is realized through the use of a solid-state thermoelectric cooler.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A two-dimensional gas chromatography system comprising:
   first and second columns;
   a thermal modulator operably disposed between said first and second columns, said thermal modulator having:

a first micro channel stage operably coupled to said first column at an inlet of said thermal modulator, a second micro channel stage operably coupled to said second column at an outlet of said thermal modulator, an interconnection channel operably coupling said first micro channel stage and said second micro channel stage, and at least one cover member covering and sealing said first micro channel stage and said second micro channel stage;

at least one rim heater operably coupled with said thermal modulator, said at least one rim heater thermal cycling said thermal modulator between a first temperature and a second temperature; and a rim portion disposed about said first micro channel stage and said second micro channel stage, said rim portion being substantially thermally isolated from said first micro channel stage and said second micro channel stage, wherein said thermal modulator trapping and focusing gas/vapor species upon said first temperature and releasing said gas/vapor species to said second column upon said second temperature.

2. The two-dimensional gas chromatography system according to claim 1 wherein said at least one rim heater is operably disposed adjacent to at least one of said inlet and said outlet of said thermal modulator, said at least one rim heater outputting thermal energy to at least one of said inlet and said outlet to inhibit vapor/gas chromatogram broadening.

3. The two-dimensional gas chromatography system according to claim 1 wherein said thermal modulator further comprises:

a first of said at least one rim heater operably disposed adjacent to said inlet and a second of said at least one rim heater operably disposed adjacent to said outlet, said first rim heater and said second rim heater outputting thermal energy to said inlet and said outlet to inhibit vapor/gas chromatogram broadening.

4. The two-dimensional gas chromatography system according to claim 1 wherein said interconnection channel defines a length in the range of 0.4 mm to 2.0 mm.

5. The two-dimensional gas chromatography system according to claim 1 wherein said interconnection channel defines a wall thickness in the range of 1 to 40 μm.

6. The two-dimensional gas chromatography system according to claim 1 wherein at least one of said first micro channel stage and said second micro channel stage defines a wall thickness in the range of 1 to 40 μm.

7. A two-dimensional gas chromatography system comprising:

first and second columns;

a thermal modulator operably disposed between said first and second columns, said thermal modulator having:

a first micro channel stage operably coupled to said first column at an inlet of said thermal modulator, a second micro channel stage operably coupled to said second column at an outlet of said thermal modulator, an interconnection channel operably coupling said first micro channel stage and said second micro channel stage, and at least one cover member covering and sealing said first micro channel stage and said second micro channel stage;

at least one rim heater operably coupled with said thermal modulator, said at least one rim heater thermal cycling said thermal modulator between a first temperature and a second temperature; and a cooling unit operably coupled adjacent to said thermal modulator defining an air gap therebetween, wherein said thermal modulator trapping and focusing gas/vapor species upon said first temperature and releasing said gas/vapor species to said second column upon said second temperature.

8. The two-dimensional gas chromatography system according to claim 7 wherein said air gap is less than 100 μm.

9. The two-dimensional gas chromatography system according to claim 7 wherein said air gap is in the range of 22 to 63 μm.

10. The two-dimensional gas chromatography system according to claim 7 wherein said cooling unit is a solid-state thermoelectric cooler.

11. The two-dimensional gas chromatography system according to claim 7 wherein said at least one cover member defines a thickness in the range of 1 to 200 μm.

12. The two-dimensional gas chromatography system according to claim 7 wherein said interconnection channel defines a length in the range of 0.4 mm to 2.0 mm.

13. The two-dimensional gas chromatography system according to claim 7 wherein said interconnection channel defines a wall thickness in the range of 1 to 40 μm.

14. The two-dimensional gas chromatography system according to claim 7 wherein at least one of said first micro channel stage and said second micro channel stage defines a wall thickness in the range of 1 to 40 μm.

15. A two-dimensional gas chromatography system comprising:

first and second columns;

a thermal modulator operably disposed between said first and second columns, said thermal modulator having:

a first micro channel stage operably coupled to said first column at an inlet of said thermal modulator, a second micro channel stage operably coupled to said second column at an outlet of said thermal modulator, an interconnection channel operably coupling said first micro channel stage and said second micro channel stage, and at least one cover member covering and sealing said first micro channel stage and said second micro channel stage; and at least one rim heater operably coupled with said thermal modulator, said at least one rim heater thermal cycling said thermal modulator between a first temperature and a second temperature;

wherein said thermal modulator trapping and focusing gas/vapor species upon said first temperature and releasing said gas/vapor species to said second column upon said second temperature and wherein said at least one heater is disposed on a common substrate with said thermal modulator.

16. The two-dimensional gas chromatography system according to claim 15 wherein said interconnection channel defines a length in the range of 0.4 mm to 2.0 mm.

17. The two-dimensional gas chromatography system according to claim 15 wherein said interconnection channel defines a wall thickness in the range of 1 to 40 μm.

18. The two-dimensional gas chromatography system according to claim 15 wherein at least one of said first micro channel stage and said second micro channel stage defines a wall thickness in the range of 1 to 40 µm.

* * * * *